United States Patent [19]

Neville, Jr. et al.

[11] 4,356,117

[45] Oct. 26, 1982

[54] CHEMICAL MODIFICATIONS OF PROTEINS WHICH INDUCE NEW RECEPTOR SPECIFICITIES AND THEREFORE ELICIT NEW EFFECTS IN CELLS

[75] Inventors: David M. Neville, Jr., Bethesda; Richard J. Youle, Kensington; Gary J. Murray, Bethesda, all of Md.

[73] Assignee: U.S. Govt., Dept. of Health & Human Services, Washington, D.C.

[21] Appl. No.: 199,781

[22] Filed: Oct. 23, 1980

[51] Int. Cl.$^3$ .............................................. C07G 7/00
[52] U.S. Cl. .............................................. 260/112 R
[58] Field of Search .................... 260/112 R; 435/240, 435/241

[56] References Cited

PUBLICATIONS

Olsnes et al.—Chem. Abst., vol. 93 (1980), p. 1892z.
Olsnes et al.—Chem. Abst., vol. 89 (1978), p. 102292b.
Eiklid et al.—Chem. Abst., vol. 93 (1980), p. 39052p.
Biochem. Biophys. Res. Commun., 45:622–628, 1971, Rogers et al.
Stowell et al., J. Biol. Chem., 253:6107–6110, 1978.
Chang et al., J. Biol. Chem., 252:1505–1514, 252:1515–1522, 1977.
Oeltmann et al., J. Biol. Chem., 254:1028–1032, 1979.
Refsnes et al., J. Exp. Med., 143:1464–1474, 1976.
Fodstad et al., Brit. J. Cancer, 34:418–425, 1976.

Primary Examiner—Sam Rosen
Attorney, Agent, or Firm—John S. Roberts, Jr.

[57] ABSTRACT

A new reagent effective in inhibiting cholesterol synthesis 75% in human fibroblasts derived from patients suffering from the disease familial hypercholestrolemia is mannose-6-phosphate-low density lipoprotein and is effective in tissue culture test systems at 100 μg/ml after a ten-hour exposure. The broad purpose of this invention is to modify the receptor specificity of a protein so that it will enter cells which were previously impermeable and exert new effects or reverse a pathological condition. Toxins may also be modified in this manner producing cell type specific and tumor suppressive reagents which are effective in a dose range of 0.3–3 μg. The object here is to use the reagent to selectively kill one cell type which is exerting a pathological effect without affecting normal cells. Among others to which this invention is applicable are Man6P-low density lipoprotein, Man6P-ricin, Man6P-Modeccin, anti Thy 1.2 monoclonal antibody-ricin and anti Thy 1.1 monoclonal antibody-

MAN6P-MODECCIN IN NORMAL HUMAN FIBROBLASTS

● MAN6P-MODECCIN ALONE
■ MAN6P-MODECCIN + LACTOSE
▲ MAN6P-MODECCIN + LACTOSE + MAN6P

PROTEIN SYNTHESIS
% CONTROL
14C - LEUCINE INCORPORATION

TOXIN CONCENTRATION (ng/ml)

FIG. 1

CHEMICAL MODIFICATIONS OF PROTEINS WHICH INDUCE NEW RECEPTOR SPECIFICITIES AND THEREFORE ELICIT NEW EFFECTS IN CELLS

This invention relates to a new reagent effective in inhibiting cholesterol synthesis 75% in human fibroblasts derived from patients suffering from the disease familial hypercholestrolemia, is a mannose-6-phosphate-low density lipoprotein and is effective in tissue culture test systems at 100 µg/ml after a ten-hour exposure. The broad purpose of this invention is to modify the receptor specificity of a protein so that it will enter cells which were previously impermeable and exert new effects or reverse a pathological condition. Toxins may also be modified in this manner producing cell type specific and tumor suppressive reagents which are effective in a dose range of 0.3–3 µg. The object here is to use the reagent to selectively kill one cell type which is exerting a pathological effect without affecting normal cells. Among others to which this invention is applicable are Man6P-low density lipoprotein, Man6P-ricin, Man6P-Modeccin, anti Thy 1.2 monoclonal antibody-ricin and anti Thy 1.1 monoclonal antibody-ricin (Thy are the murine thymic adult differentiation antigens).

The purpose of this invention is to modify the receptor specificity of a potent toxin by coupling it with a monoclonal antibody directed at a specific tumor or differentiation antigen. The object generally is to use this reagent to selectively kill human tumor cells without affecting normal cells.

A number of attempts have been made to develop tumor specific cytotoxic reagents by coupling antitumor antibodies to toxins. Early studies failed to show large selectivity between tumor cells and normal cells because (1) toxin binding to normal cells via toxin B chain was not blocked and (2) polyclonal antibodies raised in xenogenic animals have broad specificity and react with normal cells (*Science*, 169:68–70, 1970; *J. Natl. Cancer Inst.*, 55:473–477, 1975; *Nature*, 271:752–755, 1978).

These antibody toxin conjugates use the entire toxin since it is shown that the toxin B chain contains a necessary entry function in addition to its usual binding function. The toxin ricin is bound to normal cells with lactose. In animal studies antibody-ricin conjugates are given intravenously in hyperosmotic lactose, sufficient to raise serum lactose to 20–30 mM. The entry function on the toxin B chain is at an intracellular site not accessible to lactose. Therefore, the entry function is maintained and the antibody toxin conjugate in the presence of lactose has the same toxicity as ricin alone toward the target cell. To insure a high degree of tumor specific selectivity, antibodies are of monoclonal origin.

As to tumor suppressant composition used i.v. at Day 1, it has been found that an amount of 1–3 µg of anti Thy monoclonal antibody-ricin is a preferred dosage.

USE STATEMENT

The first purpose of this invention is to modify the receptor specificity of a physiologic protein with the object that the protein may gain entrance to cells which have lost their normal receptor-mediated uptake through a disease process. The new receptor entry route is chosen so that the protein exerts its normal physiologic effect through the altered receptor-uptake process. Thus mannose-6-phosphate-low density lipoprotein enters familial hypercholesterolemic fibroblasts through the mannose-6-phosphate receptor and down regulation of the rate limiting enzyme in cholesterol synthesis is achieved. This, in turn, through feedback mechanisms, may lower the elevated levels of low density lipoprotein in patients suffering from familial hypercholesterolemia.

The reagent of this invention is effective in inhibiting cholesterol synthesis by 75% in human fibroblasts derived from patients suffering from familial hypercholesterolemia, Man6P-low density lipoprotein, and is effective in tissue culture tests at 100 µg/ml.

The second purpose of this invention is to modify the receptor sepcificity of a toxin with the objective that the toxin will now bind, enter and kill a specific population of cells while leaving other cells unaffected. Thus, mannose-6-phosphate ricin in the presence of lactose selectively kills human fibroblasts while other cell types are unaffected. Monoclonal antibody toxin hybrids behave in a similar fashion.

This invention is a test or kit with some human useful linkage which utilizes an antibody toxin conjugate where the entire toxin is utilized and it is shown that the toxin B chain contains a necessary entry function in addition to its usual binding function. In animal studies antibody ricin conjugates are given intravenously in hyperosmotic lactose sufficient to raise the serum lactose to 20–30 mM.

PRIOR ART STATEMENT

Low density lipoprotein has been modified by incorporation of cationic groups and enters familial hypercholesterolemic fibroblasts and down regulates the rate limiting enzyme in cholesterol synthesis. [*Proc. Natl. Acad. Sci. USA*, 73:3178 (1976)]. Since this modification allows low density lipoprotein to bind to many receptors on many cell types, it does not constitute a cell type specific reagent and therefore has limited potential both conceptually and practically. Previous to the present construction of mannose-6-phosphate-low density lipoprotein there was no reported method for efficiently introducing functional proteins into specific cells.

The following articles describe the introduction of proteins into cell via alternate receptors. However, the internalized proteins did not affect the cell and the aim was not to achieve a functional protein operating inside the cell.
*Biochem. Biophys. Res. Commun.*, 45:622–628, 1971.
*J. Biol. Chem.*, 253:6107–6110, 1978.

The following articles were attempts to create cell type specific toxins by coupling toxin A chains with hormones. Toxicity when present was too low to be practical.
*J. Biol. Chem.*, 252:1505–1514, 1977.
*J. Biol. Chem.*, 252:1515–1522, 1977.
*J. Biol. Chem.*, 254:1028–1032, 1979.

The following is the first report of the use of lactose to block the ricin binding site of a hybrid toxin and the first report of intravenous infusions of lactose protecting mice from ricin toxicity.
*J. Exp. Med.*, 143:1464–1474, 1976.
*Brit. J. Cancer*, 34:418–425, 1976.

In the case of M6P-ricin and anti Thy 1.2 ricin hybrids, which contain the ricin B chain, these hybrids require the presence of lactose to block the ricin B chain binding to achieve cell type specificity. This limits the presently achievable selectivity between cell types to between 30- and 700-fold. Naturally occurring toxins which utilize receptor mediated protein transport systems can exhibit cell type selectivities up to 10,000-fold. This degree of selectivity could in principle be also reached by antibody-toxin hybrids of the proper construction. The currently available selectivity, however, is more than ample for the use of hybrids as selective agents for the isolation of receptor minus mutant cell lines. It may be possible to efficiently select for variants that lack any cell surface components toward which an antibody can be raised. This approach avoids utilization of complement dependent cell lysis.

The use of monoclonal antibodies as the cell recognition moiety of toxin hybrids greatly expands the possible uses of antibody-toxin hybrids. Several cell-type specific and tumor specific or tumor associated monoclonal antibodies have been produced. Hybrids of ricin with these antibodies would kill the antigen bearing cells selectively. There is considerable scientific and pharmacologic potential for these potent monoclonal antibody-ricin hybrids as cell type and tumor specific toxins.

AUTOIMMUNE DISEASES

Ricin coupled to an antigen will bind, enter and kill the specific B and T cell clones which make and regulate antibody directed toward this antigen. This will constitute a specific cure for autoimmune diseases such as myesthemia gravis, lupus erythematosus, rheumatoid arthritis, etc. Where the antigen in question is known and can be purified such as the acetylcholine receptor for myesthemia gravis, it only remains to couple the antigen to ricin and then to administer intravenously to the patient in the presence of hyperosmotic lactose sufficient to raise blood lactose to 20-30 mM. In autoimmune diseases where the antigen is unknown, such as rheumatoid arthritis, the antigen must be identified and then purified.

In retrospect, the first purpose of this invention is to modify the receptor specificity of a physiologic protein with the object that the protein may gain entrance to cells which have lost their normal receptor-mediated uptake through a disease process. The new receptor entry route is chosen so that the protein exerts its normal physiologic effect through the altered receptor-uptake process. Thus, mannose-6-phosphate-low density lipoprotein enters familial hypercholesterolemic fibroblasts through the mannose-6-phosphate receptor and down regulation of the rate limiting enzyme in cholesterol synthesis is achieved. This, in turn, through feedback mechanisms, may lower the elevated levels of low densitty lipoprotein in patients suffering from familial hypercholesterolemia.

The second purpose of this invention is to modify the receptorr specificity of a toxin with the objective that the toxin will now bind, enter and kill a specific population of cells while leaving other cells unaffected. Thus, mannose-6-phosphate ricin in the presence of lactose selectively kills human fibroblasts while other cell types are unaffected. Anti Thy 1.2-ricin also specifically kills cells carrying the Thy 1.2 antigen while leaving other cells unaffected. This reagent is active against tumors carrying Thy 1.2.

The tumor suppressive composition is active against lymphoma consisting of an injection of hybrid protein anti Thy 1.2 monoclonal antibody-ricin and hyperosmotic lactose. The inoculation i.v. of murine tissues in vivo by lymphoma is made at −20 to −25 days and the tumor suppressant composition is used i.v. at Day 1 in an amount of 1–3 μg of anti Thy monoclonal antibody-ricin together with sufficient hyperosmotic lactose to raise the lactose level to 20–30 mM. The broad purpose of this invention is to modify the receptor specificity of a potent toxin such as ricin by coupling it with a monoclonal antibody directed at a specific tumor or differentiation antigen. The object here is to use the reagent to selectively kill tumor cells without affecting normal cells.

DESCRIPTION OF THE DRAWINGS

FIG. 1 demonstrates the toxicity of the Man6P-Modeccin via the galactose route of entry (●—●), the Man6P route (■—■) and a non-specific route (▲—▲).

EXAMPLE 1

Figure 2:
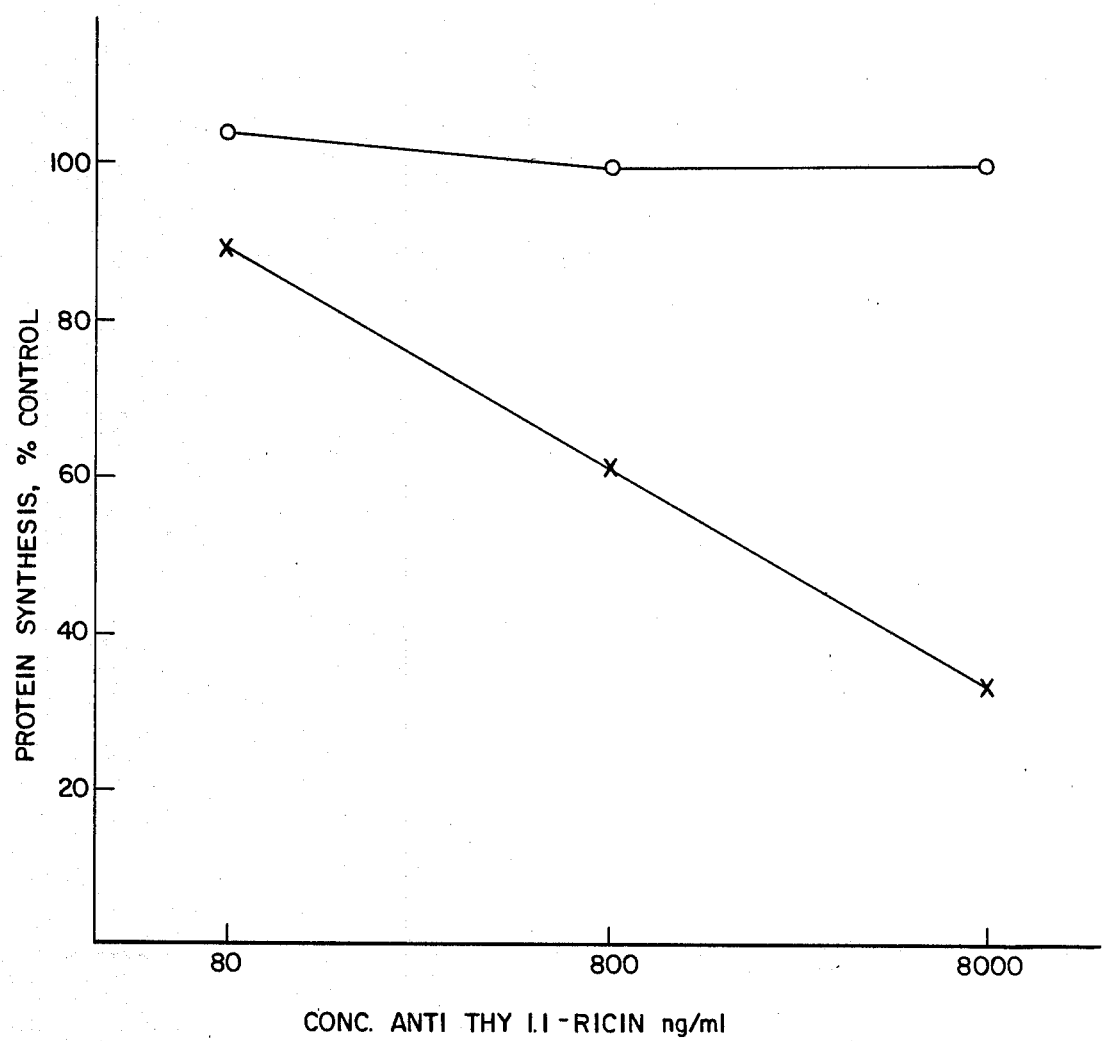
FIG. 2 demonstrates the effect of anti Thy 1.1 monoclonal antibody-ricin on the inhibition of protein synthesis on AKR-SL2 and EL-4 cells. Protein synthesis is inhibited in AKR-SL2 cells which carry the Thy 1.1 antigen. No effect is seen in this concentration range on EL-4 cells which lack the Thy 1.1 antigen. This demonstrates the cell type specificity of this reagent.

Preparation of a New Toxic Hybrid: Man6P-Modeccin

Man6P-Modeccin was prepared by covalently coupling the toxin Modeccin to ω-(6-phospho)-pentamannose. The incubation mixture consisted of: 100 μl Modeccin (3 mg/ml), 100 μl ω-(6-phospho)-pentamannose (pH 8.5, 400 mg/ml), 17 ul Bicine buffer (1-N,N-bis-hydroxy-2-ethylglycine; Calbiochem) (1.5 M, pH 9.0) and 12.5 μl [$^3$H]-NaCNBH$_3$. After 40 hours at 37° C. the mixture was passed over a column of Sephadex G-25 Superfine (0.5×25 cm) and eluted with Dulbecco's phosphate buffered saline (6.7 mM Na$_2$HPO$_4$, 15 mM NaCl) (pH 7.4). Incorporation of tritium label revealed 7 P(Man)$_5$ residues incorporated per mole of protein.

Toxicity of the Man6P-Modeccin preparation was assayed in the absence and presence of lactose and in the presence of lactose plus Man6P. The accompanying figure demonstrates the toxicity via the gal route of entry (●—●), the Man6P route (■—■) and a non-specific route (▲—▲). This is a clear demonstration of an alternate route of toxin entry via the Man6P receptor.

EXAMPLE 2

In a manner similar to the preparation of Man6P-Modeccin in Example 1, Man6P-ricin and Man6P-low density lipoprotein were prepared.

We claim:
1. A cell type specific cytotoxic reagent composition consisting of mannose-6-phosphate-Modeccin, a hybrid prepared from Modeccin.

* * * * *